(12) United States Patent
Watkins et al.

(10) Patent No.: US 6,984,497 B2
(45) Date of Patent: Jan. 10, 2006

(54) REDUCING NON-SPECIFIC BINDING IN IMMUNOASSAYS PERFORMED ON POLYMERIC SOLID PHASES

(75) Inventors: Michael I. Watkins, Vacaville, CA (US); Steven R. Binder, Berkeley, CA (US); Aleksander Raskin, Monterey, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 293 days.

(21) Appl. No.: 10/118,413

(22) Filed: Apr. 5, 2002

(65) Prior Publication Data

US 2003/0190760 A1 Oct. 9, 2003

(51) Int. Cl.
*G01N 33/53* (2006.01)

(52) U.S. Cl. ............ 435/7.92; 435/7.94; 435/962; 436/518; 436/524

(58) Field of Classification Search ............ 435/7.1, 435/7.92, 7.93, 7.94, 962; 436/501, 518, 436/524, 826
See application file for complete search history.

(56) References Cited

U.S. PATENT DOCUMENTS

| | | | |
|---|---|---|---|
| 5,358,845 A | * | 10/1994 | Horn et al. ............ 435/5 |
| 5,393,659 A | * | 2/1995 | Noah et al. ............ 435/7.94 |
| 5,658,725 A | * | 8/1997 | Schlieper et al. ............ 435/5 |
| 6,280,618 B2 | | 8/2001 | Watkins et al. |
| 6,406,858 B1 | * | 6/2002 | Petry et al. ............ 435/7.1 |

FOREIGN PATENT DOCUMENTS

WO WO 01/79844 A2 10/2001

OTHER PUBLICATIONS

Wild., The Immunoassay Handbook, Surface-coated solid-phases, pp. 59-62, M stockton press, 1994.*
Nunc Products Online Catalog, 96 MicroWell Plates catalog No. 262162, Jul. 8, 2004, www.nuncbrand.com.*
Bangs Laboratories, Inc. "Working with Microspheres," *Technote* #201 Aug. 29, 1999, pp. 1-16.

* cited by examiner

*Primary Examiner*—Long V. Le
*Assistant Examiner*—Gary W. Counts
(74) *Attorney, Agent, or Firm*—Townsend and Townsend and Crew LLP

(57) ABSTRACT

Water-soluble polymer is added to the liquid phase in a heterogeneous a immunoassay of serum, the polymer having monomers in common with monomers of the solid phase surface. This reduces non-specific binding of IgG's from the serum to the solid phase surface and thereby reduces the occurrence of false positive readings in the immunoassay.

7 Claims, No Drawings

REDUCING NON-SPECIFIC BINDING IN IMMUNOASSAYS PERFORMED ON POLYMERIC SOLID PHASES

BACKGROUND OF THE INVENTION

1. Field of the Invention

This invention resides in the field of immunoassays performed in a heterogeneous format with a polymeric solid phase. In particular, this invention addresses the problem of non-specific binding to the solid phase in serum assays and the false positive readings that are caused by such binding.

2. Description of the Prior Art

Human serum is frequently analyzed by immunoassay as a highly effective means of achieving a selective determination of serum analytes for purposes of both diagnosis and monitoring. Typical analytes determined by immunoassay include biochemical markers which when either elevated or depleted relative to their normal levels serve as indications of an abnormal physiological condition or a predilection toward disease. Other analytes include foreign substances or antibodies raised against foreign substances, either of which serves as an indication of exposure. In each case, the antigen-antibody interaction at the core of the assay provides the assay with its specificity, and the coupling of one of the binding members to a solid phase provides the assay with a highly convenient means of separating bound from unbound species.

The solid phase can assume a variety of forms and configurations, ranging from the internal walls of wells in a microtiter plate to microspheres, latex particles, or beads. A disclosure of one of the more sophisticated uses of microspheres is found in Watkins et al., U.S. Pat. No. 6,280,618 B2, dated Aug. 28, 2001, "Multiplex Flow Assays, Particularly With Magnetic Particles as Solid Phase," in which the microspheres are both magnetic and classifiable to permit a multitude of assays to be performed simultaneously on a single sample and all phase separation steps to be performed quickly and cleanly on a micro-scale with detection by flow cytometry. A disclosure of a particular multi-analyte immunoassay that can be performed in this manner is found in Bio-Rad Laboratories, Inc., International Patent Application No. WO01/79844, entitled "Multi-Analyte Diagnostic Test For Thyroid Disorders," published Oct. 25, 2001, under the Patent Cooperation Treaty. The contents of both U.S. Pat. No. 6,280,618 B2 and International Patent Application No. WO01/79844 are incorporated herein by reference in their entirety.

Certain serum samples demonstrate across-the-board positivity, i.e., a binding of IgG from the sample to the solid phase independently of the presence or absence of the analyte. This can occur both in assays in which the analyte is itself an antibody with a particular binding specificity and those in which the analyte is an antigen whose binding to the solid phase is detected by a second antibody binding. The binding of IgG, whether it be a component of the assay or extraneous serum IgG binding in a non-specific manner to the solid phase, is typically detected by labeled anti-human IgG. The non-specific IgG binding can therefore increase the reading of a positive test result, and in assays for IgG's of particular specificities, the non-specific binding can produce a positive reading when the analyte is absent, either case providing a misleading assay result.

SUMMARY OF THE INVENTION

It has now been discovered that nonspecific IgG binding to a polymeric solid phase in an immunoassay of a serum sample can be reduced by the inclusion of a water-soluble polymer in the liquid phase, the water-soluble polymer being formed by polymerization of monomers that are the same as, or have approximately the same immunological binding affinity as, monomers of the polymer at the solid phase surface. The polymer included in the liquid phase may thus be termed a "blocking agent" against non-specific IgG binding. While the two polymers have monomers in common or monomers with equivalent immunological binding affinities, they differ in water solubility, one being water-soluble (the blocking agent) and the other insoluble in water (the solid-phase polymer). Water solubility can be controlled by the presence or absence of crosslinking, by variations in molecular weight, and by copolymerization with other monomers of varying solubility characteristics. While not intending to be bound by theory, it is believed that the effectiveness of the blocking agent of this invention is attributable to its ability to mimic the solid phase by attracting the non-specific IgG by affinity binding while being soluble in the liquid phase.

DETAILED DESCRIPTION OF THE INVENTION AND PREFERRED EMBODIMENTS

Selection of the blocking agent in accordance with this invention will depend on the molecular composition of the solid phase. The solid phase will vary widely, depending on the equipment and assay protocol as well as the type of analyte. Examples of polymeric materials that can be used as the solid phase in these assays are polystyrene, polymethylmethacrylate, polybutylmethacrylate, polyvinylnaphthalene, polyvinylpyridine, polyacrylic acid, and various copolymers of these materials, particularly copolymers of styrene with vinylbenzylchloride, acrylic acid, or maleic acid, or combinations. Polystyrene and copolymers of styrene are of particular interest due to their widespread use as the solid phase, particularly as microspheres. The copolymers include random copolymers, alternating monomer copolymers, and block copolymers.

The matching of monomers between the solid phase surface and the liquid phase includes at least a portion of the monomers of each, and may include all monomers of each, but most likely will include less than all, particularly when the inclusion of additional monomers are needed to achieve water solubility. In most cases, effective results will be obtained if there is correspondence between the monomers of the water-soluble blocking agent and at least about 20% of the monomers of the polymer at the surface of the solid phase, i.e., either the monomers of the blocking agent are the same as, or have equivalent immunological binding behavior as, at least about 20% of the monomers of the solid phase polymer. More preferably, the correspondence is at least about 40%.

The phrases "equivalent immunological binding behavior" and "affinity binding behavior that is approximately the same as" are used herein interchangeably to denote approximately equal affinity strength and specificity in the types of interactions that typically constitute immunological or affinity, i.e., antigen-antibody-type, binding. The term "water-soluble" is used herein to include polymers that are freely soluble in water at essentially all proportions as well as those that of only limited solubility. Polymers of limited water solubility will be used only at concentrations well below their solubility limits.

For solid phase surfaces formed of polystyrene or a styrene-containing polymer, such as, for example, one containing at least 50% styrene, preferred water-soluble polymers are copolymers of styrene and non-styrene monomers. One example is a copolymer of styrene and acrylic acid, and another is a copolymer of styrene and maleic acid. For solid phase surfaces formed of copolymers of styrene and acrylic acid, or mixtures of polystyrene and polyacrylic acid, preferred water-soluble polymers are copolymers in which one of the monomers is either styrene or acrylic acid, or both are included.

Assays to which this invention are applicable are generally multi-step procedures involving incubation of the sample with the solid phase, followed by with re-incubation of the solid phase with other assay reagent(s) which may or may not be labeled, and detection of the occurrence of the immunological binding that indicates the presence in the sample of the analyte, the various incubation steps separated by aspiration or other forms of phase separation and repeated washings with appropriate wash buffers. In accordance with this invention, the incubation of sample with solid phase is performed in the presence of the blocking agent, and this can be achieved by adding the blocking agent to the sample before the sample is placed in contact with the solid phase, adding the blocking agent to the solid phase before the solid phase is placed in contact with the sample, or any other sequence which results in intimate contact between the sample and the blocking agent either at the same time as or before the sample and solid phase are first placed in contact. Preferably, the sample is exposed to the blocking agent before being exposed to the solid phase.

The specific amount of blocking agent to be used in the practice of this invention is not critical to the invention and may vary. Increases in the amount of blocking agent in general will provide increased blocking properties and lower non-specific binding, although each case will exhibit diminishing returns if the amount is increased beyond a certain level. This level is readily determined by routine experimentation performed by anyone skilled in immunological binding assays. Optimum concentrations of the blocking agent may vary with the selection of blocking agent, the particular type of assay being performed, the sequence of steps, and the presence or absence of other blocking agents or components in the assay medium. In most cases, best results will be obtained with a blocking agent concentration in the liquid phase ranging from about 0.003% to about 0.3% by weight, and preferably from about 0.005% to about 0.1% by weight.

In many immunoassays, the blocking agents of this invention can be supplemented to beneficial effect by conventional non-specific blocking agents, notably detergents and biological species. Typical biologically derived blocking agents are gamma globulins, such as goat, bovine, sheep, and mouse gamma globulin, proteins such as bovine serum albumin, human serum albumin, ovalbumin, and casein, and gelatins such as enzymatic gelatin hydrolysate, fish gelatin, and fish skin gelatin. Typical detergents used as blocking agents by binding hydrophobic sites on the solid phase surface are Tween 20 (fatty esters of polyoxyethylene sorbitan), Triton X-100 (octylphenol ethylene oxide condensate) and 3-[(3-cholamidopropyl)dimethylammonio]-1-propanesulfonate (CHAPS). The amounts of these agents to be used will be readily apparent to those skilled in their use in heterogeneous immunoassays.

The following examples are offered for purposes of illustration and are not intended to limit the scope of the invention.

EXAMPLE 1

This example illustrates the use of water-soluble polymeric blocking agents in an assay for anti-thyroglobulin (anti-Tg) in human serum. The assay was a flow cytometry immunoassay in which the solid phase consisted of carboxylate surface-modified polymeric magnetic particles, 8 $\mu$m in diameter, with a surface layer prepared from vinyl benzene carboxylic acids and vinyl alkyl carboxylic acids. The particles were coated with thyroglobulin (Tg) at a coating density of 1 $\mu$mg/cm$^2$. Detection of binding of anti-Tg was achieved by use of a labeled antibody consisting of phycoerythrin covalently bound to the F(Ab')$_2$ fragment of polyclonal antibody specific for human IgG. Other assay components included a particle and conjugate diluent for suspending the particles and diluting the conjugate, consisting of an aqueous solution of proteinaceous buffered saline containing detergents and preservatives, a sample of human serum that had been stripped in charcoal and was therefore negative for both anti-Tg and anti-thyroid peroxidase (anti-TPO), and a wash buffer consisting of buffered saline and detergent.

The general assay protocol consisted of combining 5 $\mu$L of the sample with 100 $\mu$L of a suspension of the particles in the particle diluent which also included a candidate blocking agent at a concentration of 0.1% by weight. The combined sample and particles were incubated for 15 minutes at 37° C., then separated by magnetic separation and washed four times with 300 $\mu$L each of wash buffer, each time followed by a three-minute magnetic separation. Labeled antibody (50 $\mu$L) was then added, and the suspension incubated for 15 minutes at 37° C., followed by washing twice with 300 $\mu$L each of wash buffer alternating with three-minute magnetic separations. The particles were then resuspended in 35 $\mu$L wash buffer and read by flow cytometry fluorescence detection.

A series of candidate blocking agents were used as well as prior art blocking agents and a blank in which no blocking agents had been added beyond those present in the sample diluent and particle diluent. For each agent and the blank, the protocol was performed twice, once with the charcoal-stripped serum as the sample and once with the wash buffer as the sample, and a relative fluorescence intensity (RFI) value was obtained for each repetition. From these values, a percent change ($\delta$), i.e., the false positive effect of the proteins in the charcoal-stripped serum as measured by the difference between the charcoal-stripped serum value and that of the wash buffer divided by that of the wash buffer, was calculated.

The blocking agents were as follows:
poly(styrene-alt-maleic acid), sodium salt: weight average molecular weight approximately 120,000
poly(acrylic acid): weight average molecular weight approximately 20,000
poly(methacrylic acid): weight average molecular weight approximately 9,500
β-lactogloblin
rabbit gamma-globulin
bovine gamma-globulin
hydrolyzed porcine gelatin
dextran
gelatin hydrolyzate
pepticase casein enzymatic hydrolase fish skin gelatin casein These results are listed in Table I below.

TABLE I

Non-Specific Binding Measurements Obtained
From Charcoal-Stripped Serum and Wash
Buffer in an Immunoassay for Anti-Tg
Using Different Blocking Agents

| | Signal (RFI) | | |
|---|---|---|---|
| Blocking Agent | Charcoal-Stripped Serum | Wash Buffer | δ (%) |
| no additional blocking agent | 366 | 180 | 103 |
| poly(styrene-alt-maleic acid) | 277 | 221 | 25 |
| poly(acrylic acid) | 330 | 229 | 44 |
| poly(methacrylic acid) | 324 | 214 | 51 |
| β-lactoglobulin | 7707 | 185 | 4066 |
| rabbit gamma-globulin | 372 | 166 | 125 |
| bovine gamma-globulin | 232 | 127 | 84 |
| hydrolyzed porcine gelatin | 337 | 174 | 94 |
| dextran | 358 | 172 | 108 |
| gelatin hydrolyzate | 321 | 164 | 96 |
| pepticase | 323 | 160 | 102 |
| casein enzymatic hydrolase | 291 | 155 | 88 |
| fish skin gelatin | 339 | 188 | 80 |
| casein | 988 | 121 | 717 |

These data demonstrate the superiority of poly(styrene-alt-maleic acid) and poly(acrylic acid) over poly(methacrylic acid) and the various biologically derived blocking agents in reducing the false positive signal. Most of the biologically derived blocking agents show no significant improvements when the charcoal-stripped serum is used, while some actually aggravated the problem by increasing the false positive signal.

EXAMPLE 2

This example illustrates the false positive signals that are obtained with assays using solid phases that contain no immunological binding member (i.e., the solid phase consists of uncoated particles) and the effect of various water-soluble polymeric blocking agents in reducing these false positive signals. A series of human serum samples were used, from both healthy subjects and subjects known to be suffering from various abnormalities. As in Example 1, the assay was a flow cytometry immunoassay using the same type of particles, but uncoated. Detection of non-specific IgG binding was achieved by use of a labeled anti-IgG antibody consisting of phycoerythrin covalently bound to monoclonal mouse antibody specific for human IgG. Other assay components included a particle diluent for suspending the particles and consisting of an aqueous solution of proteinaceous buffered saline with preservatives and detergents and a wash buffer consisting of buffered saline, preservatives and detergents. The assay protocol was the same as that set forth in Example 1.

The candidate blocking agents tested were poly(styrene-alt-maleic acid), poly(acrylic acid), poly(glutamic acid), and poly(lysine). As in Example 1, the test series includes a blank which contained no blocking agents other than those included in the sample diluent and particle diluent. The results are listed in Table II.

TABLE II

Non-Specific Binding Measurements of Various Human Serum Samples
Using Uncoated Particles and Different Blocking Agents

| | | Candidate Blocking Agent | | | |
|---|---|---|---|---|---|
| Sample and Previous Diagnosis | Blank | Poly-(styrene-alt-maleic acid) | Poly-(acrylic acid) | Poly-(glutamic acid) | Poly-(lysine) |
| (1) Scleroderma | 2043 | 225 | 931 | 2439 | 3365 |
| (2) Fatty liver, chest pain | 500 | 139 | 315 | 370 | 867 |
| (3) Fever, arthralgias | 353 | 173 | 229 | 395 | 773 |
| (4) Scleroderma | 497 | 133 | 309 | 669 | 926 |
| (5) Polymyositis | 366 | 153 | 287 | 332 | 1743 |
| (6) SLE | 2298 | 577 | 1499 | 2389 | 2375 |
| (7) Rheumatoid arthritis | 3876 | 203 | 2078 | 2457 | 8798 |
| (8) Healthy adult | 821 | 146 | 515 | 584 | 2868 |

These data demonstrate the superiority of poly(styrene-alt-maleic acid) and poly(acrylic acid) over poly(glutamic acid) and poly(lysine) in reducing the false positive signal in all samples. It is noted that poly(lysine) consistently increased the false positive signal rather than lowering it.

The foregoing is offered primarily for purposes of illustration. Further variations, modifications and substitutions beyond those mentioned herein that still embody the spirit and scope of the invention will be readily apparent to those skilled in the art.

What is claimed is:

1. In a heterogeneous immunoassay of a serum sample, one step of which consists of placing an aqueous liquid phase comprising said serum sample in contact with a solid phase comprising an immunological binding member immobilized on a polymeric water-insoluble solid support, the improvement in which said step is performed in the presence of a water-soluble polymer of a monomer that is the same as, or has affinity binding behavior that is approximately the same as, at least about 20% of the monomers from which said polymeric solid support is formed, in which said water-insoluble polymeric solid support is a polymer formed from monomers comprising styrene, and said water-soluble polymer is a copolymer of styrene and maleic acid.

2. A heterogeneous immunoassay in accordance with claim 1 in which said water-soluble polymer is poly(styrene-alt-maleic acid).

3. A heterogeneous immunoassay in accordance with claim 1 in which said water-soluble polymer is dissolved in said aqueous liquid phase at a concentration of from about 0.003% to about 0.3% by weight.

4. A heterogeneous immunoassay in accordance with claim 1 in which said water-soluble polymer is dissolved in said aqueous liquid phase at a concentration of from about 0.005% to about 0.1% by weight.

5. A heterogeneous immunoassay in accordance with claim 1 in which said aqueous liquid phase further comprises a gamma-globulin in an amount effective in reducing non-specific binding of immunoglobulin G to said solid phase.

6. A heterogeneous immunoassay in accordance with claim 1 in which said aqueous liquid phase further com prises a detergent in an amount effective in reducing non-specific hydrophobic interactions between components of said aqueous liquid phase and said solid phase.

7. A heterogeneous immunoassay in accordance with claim 1 in which said aqueous liquid phase further comprises a gamma-globulin in an amount effective in reducing non-specific binding of immunoglobulin G to said solid phase, and a detergent in an amount effective in reducing non-specific hydrophobic interactions between components of said aqueous liquid phase and said solid phase.

* * * * *